(12) United States Patent
Sevenster (10) Patent No.: US 12,136,491 B2
(45) Date of Patent: Nov. 5, 2024

(54) AI-ENABLED ECHO CONFIRMATION WORKFLOW ENVIRONMENT

(71) Applicant: KONINKLIJKE PHILIPS N.V., Eindhoven (NL)

(72) Inventor: Merlijn Sevenster, Haarlem (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 643 days.

(21) Appl. No.: 17/439,853

(22) PCT Filed: Mar. 18, 2020

(86) PCT No.: PCT/EP2020/057360
§ 371 (c)(1),
(2) Date: Sep. 16, 2021

(87) PCT Pub. No.: WO2020/187952
PCT Pub. Date: Sep. 24, 2020

(65) Prior Publication Data
US 2022/0189633 A1 Jun. 16, 2022

Related U.S. Application Data

(60) Provisional application No. 62/820,892, filed on Mar. 20, 2019.

(51) Int. Cl.
*G16H 50/00* (2018.01)
*A61B 8/08* (2006.01)
(Continued)

(52) U.S. Cl.
CPC ........... *G16H 50/20* (2018.01); *A61B 8/0883* (2013.01); *A61B 8/5223* (2013.01);
(Continued)

(58) Field of Classification Search
CPC ...... G16H 50/20; G16H 30/20; A61B 8/0833; A61B 8/5223; G06F 3/0482;
(Continued)

(56) References Cited

U.S. PATENT DOCUMENTS 6,785,410 B2    8/2004  Vining et al.
7,244,230 B2    7/2007  Duggirala et al.
(Continued)

FOREIGN PATENT DOCUMENTS

CA    3124755 A1 *  7/2020  ............. A61B 5/364

OTHER PUBLICATIONS

PCT/2020/057360 ISR & Written Opinion, Jun. 8, 2020.
Zhang et al"Fully Automated Echocardiogram Interpretation in Clinical Practice"; Circulation, 2018, vol. 138, pp. 1623-1635.

*Primary Examiner* — Khai M Nguyen (57) ABSTRACT

In an echocardiogram analysis method, a diagnostic code is received or generated for an echocardiogram comprising a set of echocardiogram loops. A plurality of different subsets are selected from the echocardiogram. Each subset consists of one or more echocardiogram loops of the set of echocardiogram loops. For each subset, a confidence score indicating relevance of the subset to the diagnostic code is determined using an artificial intelligence (AI) engine operating on the subset, where the AI engine is trained on historical echocardiograms labeled with diagnostic codes. A relevant group of echocardiogram loops is identified based on the determined confidence scores for the respective subsets indicating relevance of the respective subsets to the diagnostic code. An echocardiogram reading user interface is presented, including displaying the diagnostic code associated with the echocardiogram loops of the relevant group of echocardiogram loops.

15 Claims, 6 Drawing Sheets

(51) Int. Cl.
*G06F 3/0482* (2013.01)
*G06F 3/0484* (2022.01)
*G06T 7/00* (2017.01)
*G16H 30/20* (2018.01)
*G16H 50/20* (2018.01)

(52) U.S. Cl.
CPC .......... *G06F 3/0482* (2013.01); *G06F 3/0484* (2013.01); *G06T 7/0012* (2013.01); *G16H 30/20* (2018.01); *G06T 2200/24* (2013.01); *G06T 2207/10132* (2013.01); *G06T 2207/30048* (2013.01)

(58) Field of Classification Search
CPC . G06F 3/0484; G06T 7/0012; G06T 2200/24; G06T 2207/10132; G06T 2207/30048
See application file for complete search history.

(56) References Cited

U.S. PATENT DOCUMENTS

| | | |
|---|---|---|
| 7,744,540 B2 | 6/2010 | Rao et al. |
| 8,280,750 B2 | 10/2012 | Krishnan et al. |
| 8,295,576 B2 | 10/2012 | Gadodia et al. |
| 11,864,944 B2 * | 1/2024 | Fornwalt ................ A61B 8/065 |
| 2006/0064017 A1 | 3/2006 | Krishnan et al. |
| 2013/0096447 A1 | 4/2013 | Dhawan et al. |
| 2019/0026437 A1 * | 1/2019 | Syeda-Mahmood .. G16H 50/70 |
| 2021/0052252 A1 * | 2/2021 | Hare, II .................... G06T 7/11 |

\* cited by examiner

| Information | Measure | Score | Interpret | Comments |

| LV | RV | Altria | MV | TV |
| AV | PV | Great vessels | | PE |

Finding code

[ ] [Run auto pop] [Run rules]

ac00:LV size/shape

LV:0061 grossly normal size ac00:LV thrombus/VSD

LV:0125 Apical thrombus, moderate size
LV:0129 thrombus appears mobile ac00:LV thickness LV:0066 global thinning ac00:LV function ac00:LV wall motion FIG. 4
(Continued)

FIG. 5

AI-ENABLED ECHO CONFIRMATION WORKFLOW ENVIRONMENT

CROSS-REFERENCE TO PRIOR APPLICATIONS

This application is the U.S. National Phase application under 35 U.S.C. § 371 of International Application No. PCT/EP2020/057360, filed on Mar. 18, 2020, which claims the benefit of U.S. Provisional Patent Application No. 62/820,892, filed on Mar. 20, 2019. These applications are hereby incorporated by reference herein.

FIELD

The following relates generally to the cardiology arts, echocardiography arts, cardiac imaging arts, and related arts.

BACKGROUND

Echocardiograms are a common cardiologic imaging modality. The number of diagnoses that can be obtained from an echocardiogram is relatively small compared to general radiology. In the order of 50 diagnoses can be derived from echocardiography studies. In the echocardiography examination, the technician acquires echocardiogram loops, which are short time sequences of ultrasound images usually spanning one or a few heartbeats. These are acquired at different positions (i.e. "views") of the ultrasound transducer (respective to the heart) There are a few standard views (e.g. around 8), and for each standard view various cardiology groups may recognize up to around a dozen sub-views. Each loop is typically acquired with the ultrasound transducer probe manually positioned by the ultrasound technician on the torso of the patient at an angulation respective to the heart suitable for imaging the desired view/sub-view. The image quality of any given loop can vary significantly depending on the steadiness with which the technician holds the ultrasound transducer probe and the extent to which the patient may move during acquisition of the loop. Additionally, the "quality" of a view depends on how accurately the technician properly positioned the ultrasound transducer probe for that view. The technician can observe the acquired loop on a display of the ultrasound machine, and may acquire multiple loops for a given view depending on the technician's subjective opinion of the loop image quality and how well the acquired loop visualizes the desired view.

A preliminary report is sometimes made by the technician by reviewing the ultrasound loops and entering diagnostic codes or diagnostic language that is clinically straightforward to interpret. The technician is not a trained cardiologist, and accordingly commonly avoids making non-trivial diagnoses. The loops along with metadata such as the preliminary diagnoses are stored at a Picture Archiving and Communication System (PACS), Cardiovascular Information System (CVIS), and/or other electronic database(s). At a later time, a cardiologist reviews the echocardiogram, typically using any preliminary diagnoses provided by the technician as a starting point.

The following discloses certain improvements.

SUMMARY

In some non-limiting illustrative embodiments disclosed herein, a non-transitory storage medium stores instructions readable and executable by an electronic processor to perform an echocardiogram analysis method including generating or receiving a diagnostic code for an echocardiogram comprising a set of echocardiogram loops. A plurality of different subsets are selected from the echocardiogram. Each subset consists of one or more echocardiogram loops of the set of echocardiogram loops. For each subset, a confidence score indicating relevance of the subset to the diagnostic code is determined. The confidence score is determined using an artificial intelligence (AI) engine operating on the subset, where the AI engine is trained on historical echocardiograms labeled with diagnostic codes. A relevant group of echocardiogram loops is identified based on the determined confidence scores for the respective subsets indicating relevance of the respective subsets to the diagnostic code. An echocardiogram reading user interface is presented, including displaying the diagnostic code associated with the echocardiogram loops of the relevant group of echocardiogram loops.

In some non-limiting illustrative embodiments disclosed herein, an echocardiogram analysis device includes an electronic processor and a non-transitory storage medium, which stores instructions readable and executable by the electronic processor to analyze an echocardiogram comprising a set of echocardiogram loops. The stored instructions include: AI engine instructions implementing an AI engine trained to output confidence levels for diagnostic codes in response to receiving an input set of one or more echocardiogram loops; relevant loops identification instructions implementing a relevant loops identification including determining confidence levels for a preliminary diagnostic code for different subsets of the set of echocardiogram loops by inputting the different subsets to the AI engine and identifying a relevant group of echocardiogram loops based on the determined confidence scores for the respective subsets; and echocardiogram reading instructions implementing an echocardiogram reading user interface on a client system including displaying, on a display of the client system, the preliminary diagnostic code associated with the echocardiogram loops of the relevant group of echocardiogram loops.

In some non-limiting illustrative embodiments disclosed herein, an echocardiogram analysis method is disclosed, which utilizes an AI engine trained to output confidence levels for diagnostic codes in response to receiving an input set of one or more echocardiogram loops. The echocardiogram analysis method includes: generating or receiving a preliminary diagnostic code for an echocardiogram comprising a set of echocardiogram loops; determining confidence levels for the preliminary diagnostic code for different subsets of the set of all echocardiogram loops by inputting the different subsets to the AI engine and identifying a relevant group of echocardiogram loops that are relevant to the preliminary diagnostic code based on the determined confidence scores for the respective subsets; and presenting an echocardiogram reading user interface including displaying, on a display of a client system, the preliminary diagnostic code associated with the echocardiogram loops of the relevant group of echocardiogram loops.

One advantage resides in providing a more efficient user interface for echocardiogram interpretation environment.

Another advantage resides in providing a user interface for an echocardiogram interpretation environment that reduces the number of loops of an echocardiogram that must be reviewed in order to make or confirm a given diagnostic code.

Another advantage resides in providing a user interface via which a cardiologist can confirm a previously generated diagnosis instead of creating a diagnosis from scratch.

Another advantage resides in providing a user interface for an echocardiogram interpretation environment that reduces the number of less relevant or irrelevant loops that are considered by a cardiologist or other user in making or confirming a given diagnostic code.

Another advantage resides in providing automated preliminary diagnostic capability for analyzing an echocardiogram in an echocardiogram interpretation environment.

Another advantage resides in providing a user interface for an echocardiogram interpretation environment that reduces a likelihood of failing to consider a relevant loop that is mislabeled as to view (or sub-view) in making a clinical diagnosis.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
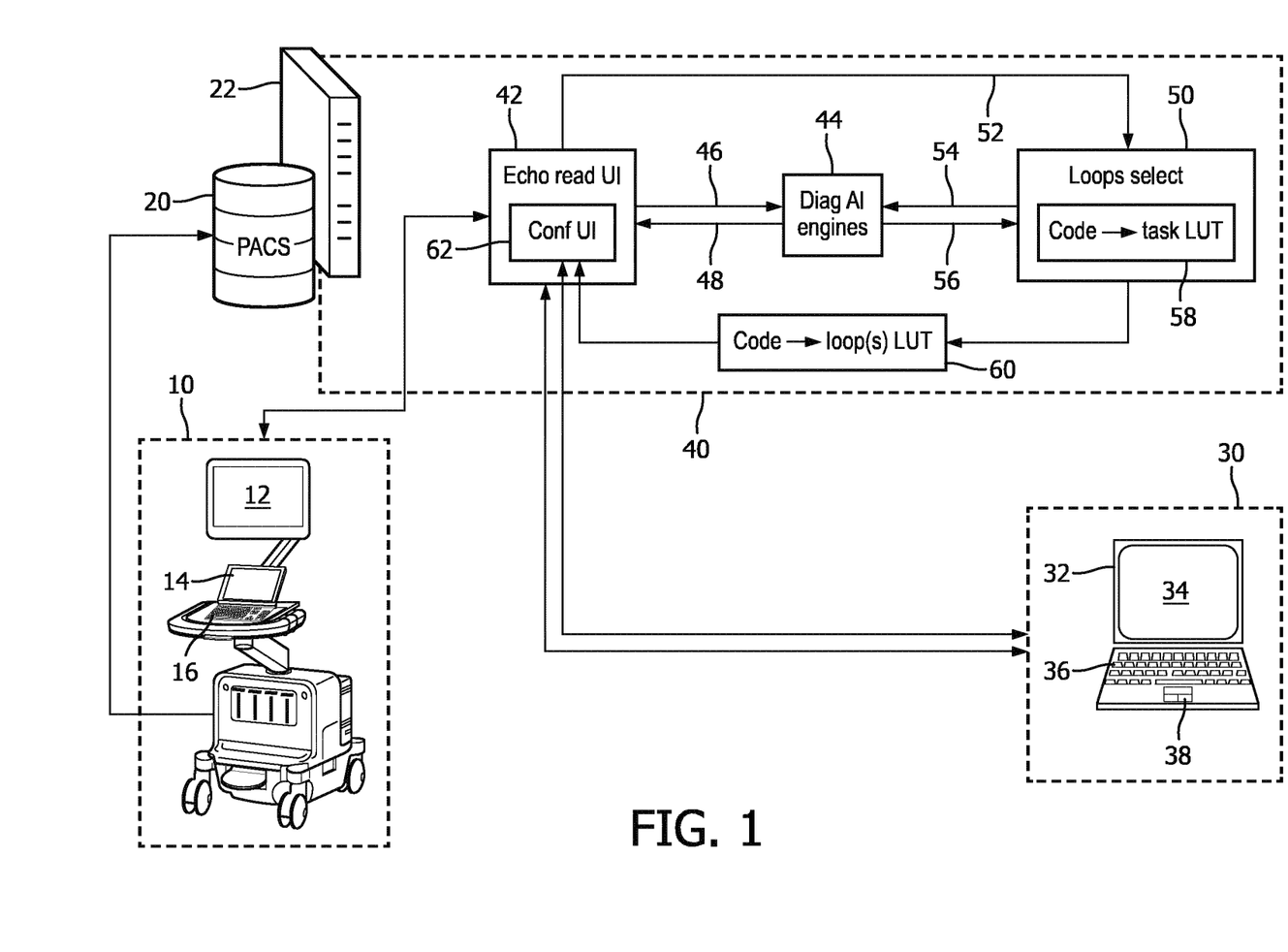
FIG. 1 diagrammatically illustrates an echocardiogram acquisition and reading system.

With reference to FIG. 1, an echocardiogram acquisition and reading system is diagrammatically shown. The illustrative system includes an echocardiogram acquisition device 10, which is typically a cardiac ultrasound imaging system (i.e. echocardiograph) 10 programmed to acquire echocardiogram loops (also referred to herein as a "loop" for brevity), which are short time sequences of ultrasound images of the heart (and/or a major cardiac blood vessel) usually spanning one or a few heartbeats. These are acquired at different positions (i.e. "views") of the ultrasound transducer probe (not shown) respective to the heart. Typically, each loop is acquired with the ultrasound transducer probe manually positioned by the ultrasound technician on the torso of the patient at an angulation respective to the heart suitable for imaging the desired view/sub-view. The echocardiograph 10 includes at least one display 12, 14 (in the non-limiting illustrative example, a main display 12 for displaying ultrasound images or playing back ultrasound loops, and a user interface display 14 for presenting operating parameter values or the like) and one or more user input devices 16 such as a keyboard, trackpad, touch-sensitive overlay of one or both displays 12, 14, and/or so forth, In a typical echocardiogram study acquisition session, an ultrasound technician places the probe at an appropriate position on the patient's chest to acquire a view of the heart. The acquired echo is played on the display 12. If the loop is not satisfactory to the technician, he or she may reposition the probe and/or ask the patient to remain still, and then acquire another loop capturing the view. This may be repeated multiple times for a given view, and/or the probe position may be adjusted to acquire various sub-views of the view. Typically, all acquired loops are saved to a PACS 20 (and/or to a CVIS or other electronic database), unless they are of obviously nonclinical quality.

While acquiring the loops, and/or after the loops are acquired, the technician usually performs a preliminary analysis to draw preliminary findings and/or diagnoses. These are usually represented using a standard notation in which a given finding or diagnosis is represented by a diagnostic code (also referred to herein as a "code" for brevity). A diagnostic code is a unique identifier corresponding to a certain diagnosis or finding, which may encompass a disease and/or its severity state (e.g. normal/mild/moderate/severe). Diagnostic codes can also be defined which convey that a certain diagnosis cannot be assessed reliably, for example because of limited image quality. The preliminary diagnostic codes are stored with the echocardiogram loops at the PACS 20 in a suitable echocardiogram study data package, and the preliminary diagnostic codes are later confirmed, rejected, or modified by a cardiologist who reviews the echocardiogram, and who may also add additional diagnostic codes representing additional findings or diagnoses made by the cardiologist.

In a common implementation, an echocardiogram interpretation environment is hosted by a server computer 22, which may optionally also host the PACS 20 and/or other electronic database that stores the echocardiogram loops. In general, the server computer 22 may be a single server computer (or desktop computer or other computer with sufficient processing capability) or a plurality of computers configured as a computing cluster, cloud computing resource, or so forth. The echocardiogram interpretation environment is accessed by client systems, such as the illustrative echocardiograph 10, a cardiologist's workstation 30, and/or so forth. The illustrative cardiologist's workstation 30 includes a computer 32 with at least one display 34 and one or more user input devices such as a keyboard 36, trackpad 38 (and/or mouse and/or other pointing device), and/or so forth. The client systems 10, 30 are illustrative examples, and a typical cardiology department of a hospital or other medical facility may have several dozen or more devices capable of accessing the echocardiogram interpretation environment as client systems. Typically, most of the data processing for implementing the echocardiogram interpretation environment is executed at the server 22, although some less computationally intensive processes (e.g. rendering of a user interface display) and/or specialized processes (e.g. controlling the ultrasound hardware of the echocardiograph 10 to acquire an echocardiograph loop) may be performed locally at the client system 10, 30. The user interface of the echocardiogram interpretation environment that is presented on a given client system may depend on numerous factors such as the credentials of the client system (e.g., a user identification of the user logged into the client system, often having associated access/privilege levels) and the capabilities of the client system (e.g., a user accessing the echocardiogram interpretation environment by way of the echocardiograph 10 may be provided with a user interface supporting loop acquisition; whereas the cardiologist's workstation 30 may not provide these loop acquisition user interface aspects). Typically, the cardiologist's workstation 30 will provide the user (e.g. cardiologist) with access to any preliminary diagnostic codes entered by the technician at the echocardiograph 10. By way of non-limiting illustrative example, the echocardiogram interpretation environment may be the Philips Intelli Space Cardiovascular (ISCV)™ echocardiogram interpretation environment available from Koninklijke Philips N.V. (with additional features provided as disclosed herein).

In order to perform the review of the preliminary diagnostic codes determined by the technician, the cardiologist must review the various acquired loops of the echocardiogram in order to identify the most relevant loops for confirming or rejecting each preliminary diagnostic code. While the loops may be labeled by view, and perhaps also by sub-view, this is not necessarily enough for the cardiologist to efficiently and comprehensively select the best views for confirming a diagnostic code. The loop acquisition is a semi-manual process insofar as the technician manually places the ultrasound transducer probe externally on the torso of the patient, and the image quality of any given loop depends on the precise placement of the transducer probe and the amount of motion blurring (the motion may be unsteadiness in holding the probe, or movement by the patient, or both). The technician may therefore acquire several loops for any given view, which may be of varying image quality and which may provide more or less ideal vantage for the view (e.g., some loops may be recorded with the transducer probe at a less than ideal position for capturing the intended view). Furthermore, the view labels assigned to the various loops could be in error. As a result, selection of the "best" views for confirming a given diagnosis is tedious, potentially subjective, and can be prone to error.

Artificial intelligence (AI), such as a convolutional neural network (CNN) trained on echocardiograms annotated with diagnostic codes supplied by readings performed by expert cardiologists, has the potential to improve the echocardiogram readings. However, such AI may not be sufficiently reliable to perform fully automated diagnosis of an echocardiogram. Unless the AI can be made sufficiently reliable to perform fully automated diagnosis, a cardiologist will still need to review the preliminary diagnostic codes (whether human- or AI-generated), and hence the above-outlined problems are not alleviated. Given the life-critical nature of ensuring accurate echocardiogram readings, in many situations it may not be practical to replace the expertise of the cardiologist in reading an echocardiogram by AI analysis of the echocardiogram.

In view of the above-outlined matters, embodiments disclosed herein leverage AI analysis of echocardiograms in a way that provides improved efficiency and accuracy in the echocardiogram reading workflow, without relying upon the AI to provide a definitive diagnosis.

In one aspect disclosed herein, AI is used to generate preliminary diagnostic codes, either replacing or augmenting the preliminary analysis performed by the technician. Optionally, the AI may also assign confidence scores to the generated diagnostic codes. As these are only preliminary diagnostic codes, the potential for error by the AI is of less concern as the preliminary diagnostic codes will be reviewed by a skilled cardiologist.

In another aspect disclosed herein, AI is used to select the most relevant loops for reviewing preliminary diagnostic codes. In other words, starting with a preliminary diagnostic code (generated by a human, such as the ultrasound technician, or by AI), a candidate loop is input to the AI which outputs the diagnostic code (if indeed the AI associates the loop with the diagnostic code) and also outputs the confidence score for the diagnostic code. This metric or metrics quantify relevance of the loop to the diagnostic code. For example, if the code is output by the AI for the loop with high confidence then the loop is highly relevant; whereas, if the code is not output at all by the AI, or is output by the AI but with a low confidence score, then the loop is not very relevant.

By such metrics, the loops of the echocardiogram can be ranked as to relevance to a given diagnostic code. In one formal approach, a table is generated of the preliminary diagnostic codes and for each code the relevant loops represented (for example) as the set of up to N loops with relevance to the code which is higher than some threshold. In some variant embodiments, the relevant loop selection operates iteratively. For example, if there are 99 loops in the echocardiogram, then each loop is initially input to the AI along with a diagnostic code, and the most relevant loop to that diagnostic code is identified. Then, that most relevant loop is combined in succession with each of the remaining 98 loops to identify the second most relevant loop. Then, those two most relevant loops are combined in succession with each of the remaining 97 loops to identify the third most relevant loop. This can be repeated to generate a ranked list of (in general, N) most relevant loops The operation of the AI may employ various inputs and outputs. For example, in some embodiments, a diagnostic code is input to the AI along with one or more loops, and only a single metric is output by the AI for that input code, namely a confidence score for the code. In this approach, the code is an input to the AI, and a sufficiently low confidence score output by the AI for the code may be understood by a human reviewer as indicating that the AI is not recommending the diagnostic code.

In other illustrative embodiments, the diagnostic code is not an input—rather, only the loop or loops are input to the AI. In these embodiments, the AI processes the loop(s) to determine whether they support various diagnostic codes, and outputs a diagnostic code along with its confidence score only if its confidence score is above some threshold. In these embodiments, the diagnostic code is an output rather than an input.

Furthermore, it is to be appreciated that the confidence score for a diagnostic code, as used herein, is to be broadly construed as a metric of how likely it is that the patient imaged by the processed loop(s) has the diagnosis or finding indicated by the diagnostic code, according to the AI analysis of the loop(s). The confidence score may, for example, be variously expressed as a percentage (e.g, in a range [0%, 100%]) or probability (e.g. in a range [0,1]) where a confidence score of close to 100% (or probability close to 1) corresponds to a very high likelihood that the patient has the diagnosis or finding indicated by the code, whereas a score of close to 0% (or probability close to 0) corresponds to a very low likelihood. As another example, the confidence score for a code may be monotonically increasing with increasing likelihood that the patient has the diagnosis or finding indicated by the code, but the range of potential confidence score values may be other than 0-100%. These are merely illustrative examples.

The two aspects of (1) providing a preliminary diagnostic code by AI analysis, and (2) selecting the most relevant loops by AI analysis, are independent. For example, in some embodiments only the first aspect is employed: AI is used to generate the preliminary codes but is not used to select the most relevant loops for the AI-generated preliminary codes. In other embodiments, only the second aspect is employed: the preliminary diagnostic codes are generated manually (e.g., by a technician reviewing the loops) and AI is used only to select the most relevant loops for the manually generated preliminary diagnostic code.

In yet other embodiments, the first and second aspects are employed together. That is, some or all of the preliminary diagnostic codes may be generated by the AI according to the first aspect, and then AI is used to select the most relevant loops for a preliminary diagnostic code (regardless of whether the preliminary diagnostic code was selected manually or by AI according to the first aspect). Advantageously, in such embodiments combining the first and second aspects, the same AI engines may be employed for both the first aspect (generating some or all preliminary diagnostic codes) and the second aspect (selecting the most relevant loops for manually reviewing the diagnostic codes).

Embodiments which employ AI to select the most relevant loops for a given preliminary diagnostic code may optionally employ an improved user interface for the echo interpretation environment via which the cardiologist reviews preliminary diagnostic codes. In the user interface, the preliminary diagnostic codes are listed, each associated with the most relevant loops for that code. The association of the relevant loops with the code can be direct, e.g. displaying the most relevant loops for that code, or can be associated by way of displaying hyperlinks to the most relevant loops stored in the PACS 20 (where the hyperlinks are optionally represented by thumbnail images or thumbnail videos representing the loops). The confirmation user interface further provides a "Confirm" button (or other suitable user-selectable dialog element) by which the cardiologist can select to confirm a preliminary diagnostic code. In embodiments in which hyperlinks or thumbnails are displayed to represent the relevant loops, the cardiologist can click on a loop to bring up a larger video showing the loop at its full resolution. If the cardiologist selects the "Confirm" button, then the confirmed diagnostic code is added to the echocardiogram report as the diagnostic code and/or as a corresponding natural language text statement of the finding or diagnosis represented by the diagnostic code. Optionally, links to the most relevant loops may also be automatically annotated to the diagnostic code in the report.

Some embodiments may also employ the AI to select the most relevant loops for a diagnostic code chosen by the cardiologist (or, by the technician during the preliminary diagnosis stage). For example, the cardiologist (or technician) may be reviewing a given loop or set of loops, and may enter a diagnostic code based on the cardiologist's reading of those loops (or may enter a preliminary code based on the technician's reading, in the preliminary phase). This cardiologist- or technician-entered diagnostic code is then immediately input to the relevant loops selection engine which identifies the most relevant loops for that diagnostic code. If an AI-selected highly relevant loop is not presently being reviewed by the cardiologist (or technician), then a user dialog is opened to suggest review of that additional loop.

In another contemplated aspect, AI engines may also be trained to identify loops that are highly contra-indicative of a given diagnostic code (that is, trained to identify loops that strongly suggest that the diagnostic code is not appropriate for this echocardiogram study), and if a highly contra-indicative loop is identified then a user dialog is opened to suggest that the cardiologist review that contra-indicative loop.

With continuing reference to FIG. 1, an echocardiogram interpretation environment 40 is diagrammatically illustrated, which is suitably implemented by instructions stored on the non-transitory storage medium 20 which are read and executed by the electronic processor 10, 22, 30. In a typical setup, the server 22 performs the more complex processing to implement the interpretation environment 40, such as implementing neural networks, support vector machine (SVM) classifiers, or other complex AI, while local processors at (or comprising) client systems such as the echocardiograph 10 or the cardiologist's workstation 30 perform user interface dialog rendering operations, local control of the ultrasound image acquisition hardware, data entry of a cardiogram report, and/or so forth. The echocardiogram interpretation environment 40 includes an echocardiogram reading user interface (UI) 42, which may, by way of one non-limiting example, be implemented as the UI of the Philips IntelliSpace Cardiovascular (ISCV)™ echocardiogram interpretation environment. The echocardiogram interpretation environment 40 further includes one or more diagnostic AI engines 44 which receive one or more loops and in response output diagnostic codes and associated confidence scores (or, in a variant embodiment, receive one or more loops and a diagnostic code and output only the confidence score for that diagnostic code). In embodiments which include AI-generated preliminary diagnostic codes, implementation of such preliminary AI diagnosis entails inputting one or more loops 46 to the AI engine(s) 48 and receiving back one or more preliminary diagnostic code(s) 50 (preferably along with corresponding confidence scores) in response.

The echocardiogram interpretation environment 40 further includes a (most relevant) loops selection component 50 that identifies the most relevant loops in an echocardiogram for a given input diagnostic code 52. To do so, the loops selection component 50 inputs one or more loops 54 to the AI engine(s) 44, optionally along with a diagnostic code (in embodiments for which the AI receives the code as an input) or along with a task identification (in embodiments in which the AI does not receive a code but in which there are a plurality of AI engines trained to perform different tasks, the supplied task identification effectively determines which AI engine or engines should be employed). As one non-limiting illustrative example, a task may be a left ventricle assessment task, and a corresponding AI engine 44 may be trained to output an appropriate diagnostic code given the input loop(s), such as one of the codes selected from the group: LV-1: Left ventricular performance is normal; LV-2: Left ventricular performance is mildly reduced; LV-3: Left ventricular performance is moderately reduced; LV-4: Left ventricular performance is severely reduced; LV-Q: Cannot assess left ventricular performance because of low image quality; and LV-I: Cannot assess left ventricular performance because of incomplete study. In response to the input(s) 54 supplied by the loops selection component 50, the AI engine(s) 44 return a result 56 including the diagnostic code or codes generated by the AI along with corresponding confidence score(s) (or, in the alternative embodiment in which the code is an input, the result 56 may be only the confidence score determined for that code by the AI). For embodiments in which the AI engine(s) 44 are task-oriented, the loops selection component 50 suitably includes a diagnostic code-to-task conversion look-up table 58. For example, if the received code 52 is LV-2 then in the previous example the table 58 will associate the code LV-2 to the left ventricular performance task. Based on the returned confidence scores 56 for the input diagnostic code 52, the loops selection component 50 identifies the most relevant loops for the code 52. By performing this process for various preliminary diagnostic codes, the loops selection component 50 builds up a look-up table 60 associating each preliminary diagnostic code with a set of most relevant loops. A confirmation UI 62 (or sub-UI 62) of the echocardiogram reading UI 42 presents the preliminary diagnostic codes to the cardiologist at the workstation 30 along with the most relevant loops for each code as identified in the look-up table 60 constructed by the loops selection component 50.

Figure 2:
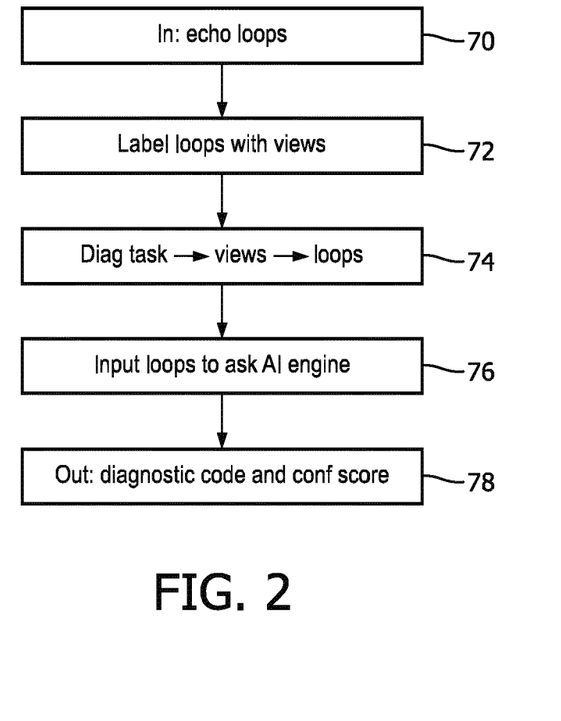
FIG. 2 diagrammatically illustrates a flowchart of a process for automatically analyzing one or more loops of an echocardiogram to detect whether the loop(s) indicate a certain a diagnostic code, which is suitably performed by the system of FIG. 1.

With reference to FIG. 2, one possible illustrative workflow for generating preliminary diagnostic codes using the AI engine(s) 44 is of FIG. 1 is shown. In an operation 70, echo loops are received (e.g. acquired by the echocardiograph 10 for a patient undergoing a cardiogram). In an operation 72, the loops are labeled as to view (and optionally also sub-view). The operation 72 may be a manual operation performed by the ultrasound technician, or an automated labeling using a loop classifier, or some combination of these. In an operation 74, a diagnostic task is chosen, and the appropriate view(s) identified and loops of the echocardiogram labeled at 72 with those view(s) are selected. For performing a preliminary diagnosis, the output of operation 74 is the input 46 shown in FIG. 1. For example, if the ultrasound technician is requesting AI assistance in performing a left ventricular (LV) assessment, the technician selects the LV assessment task, and a look-up table is referenced to identify the standard views for performing an LV assessment. The loops of the echocardiogram labeled with those views then form the input 46 to the AI engine(s) 44. At operation 76 of FIG. 2, the loop(s) chosen at operation 74 are input to the AI engine(s) 44, possibly along with an identification of the task if that is an input for the AI engine(s) 44 (e.g. to select to use the specific AI engine trained to perform that task). At operation 78, the diagnostic code (or codes) generated by the AI engine(s) 44 in response to the input 76 are received and, for example, displayed for consideration by the technician on the display 14 of the echocardiograph 10. As another option, the AI-generated code(s) output at operation 78 may be automatically entered into the preliminary echocardiogram report, or may be so entered after confirmation by the ultrasound technician. In the case of automatic insertion into the report, such automatic insertion may only be done if the confidence score is above some minimum threshold (e.g. >80% confidence).

Figure 3:
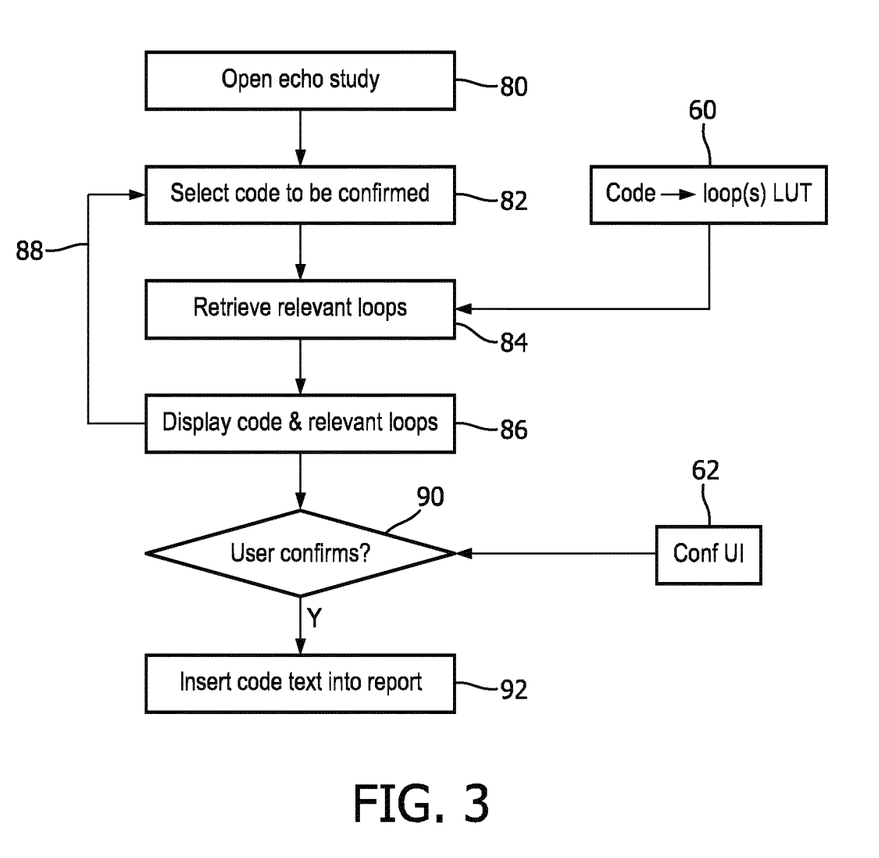
FIG. 3 diagrammatically illustrates a flowchart of a process for reviewing and confirming diagnostic codes during review of an echocardiogram, which is suitably performed by the system of FIG. 1.
Figure 4:
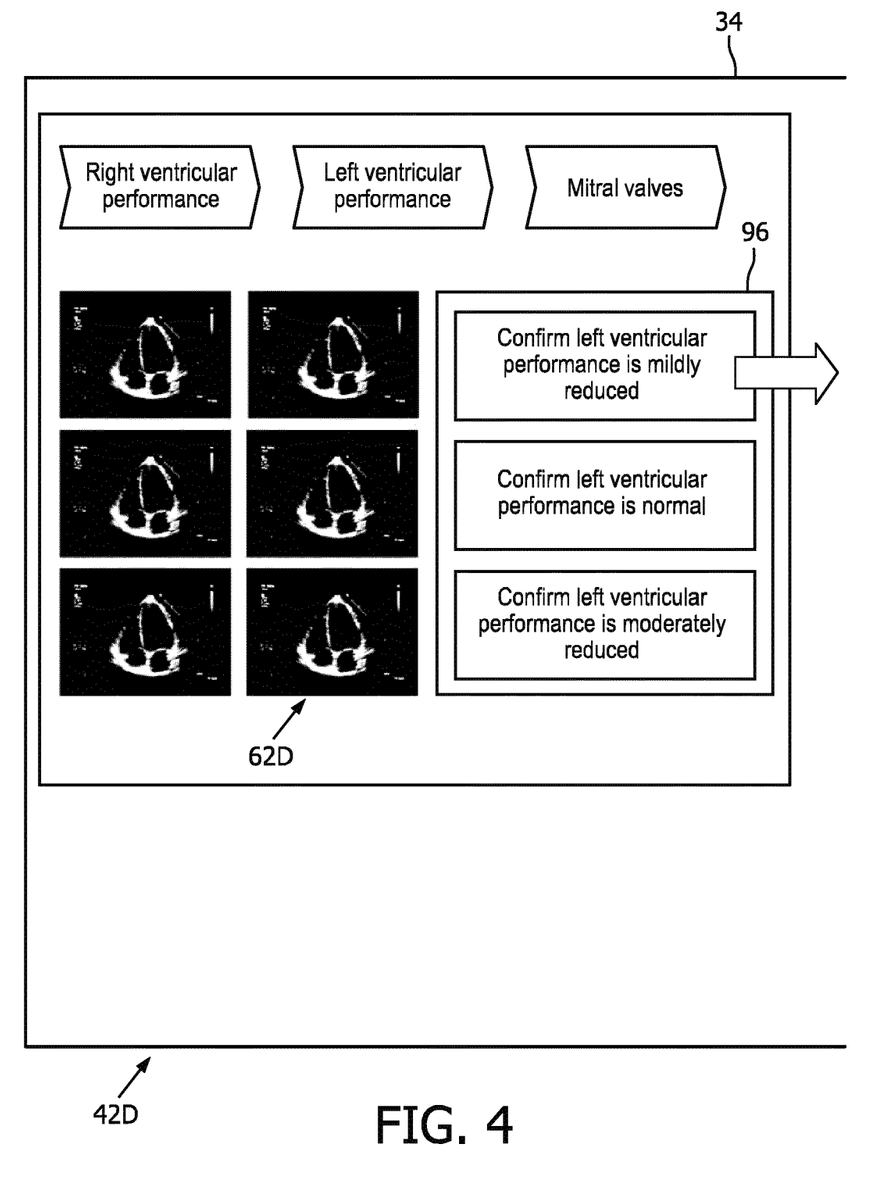
FIG. 4 diagrammatically illustrates a user interface display suitably presented by the system of FIG. 1 when performing the method of FIG. 3.

With reference to FIGS. 3 and 4, an illustrative confirmation process via which the cardiologist confirms preliminary diagnostic codes assisted by the confirmation UI 62 backed by the loops selection component 50 is described. In an operation 80, the echocardiogram study is retrieved to the cardiologist's workstation 30. The retrieved echocardiogram includes various preliminary diagnostic codes generated by the ultrasound technician and/or by the AI engine(s) 44, e.g. via the method of FIG. 2. This information is suitably displayed on the display 34 of the cardiologist's workstation 30 as a display 42D (non-limiting illustrative display example shown in FIG. 4) of the echocardiogram reading UI 42. The display 42D includes a display window 62D generated by the confirmation UI 62. To produce this display 62D, in an operation 82 a preliminary code to be confirmed is selected; in an operation 84 the look-up table 60 is referenced to identify the most relevant loops for the code selected at 82 (again, the look-up table is generated by the loops selection component 50 as previously described with reference to FIG. 1); and in an operation 86 the code is displayed in association with the relevant loops. As indicated by looping arrow 88, this sequence may be repeated for each preliminary diagnostic code. This information is presented in FIG. 4 as the illustrative confirmation display window 62D, including selection buttons to select preliminary codes for the left ventricular (LV) performance being mildly reduced, normal, or moderately reduced, with the two most relevant loops for each of these three codes shown to the left of each code selection box. In the illustrative example, each of the loops is represented as a thumbnail of one frame of the loop; however, other representations can be employed, for instance if the workstation 30 has sufficient computing power the loops could be running (i.e. shown as thumbnail videos). While two most relevant loops are shown for each preliminary diagnostic code in the confirmation display window 62D of FIG. 4, the number of most relevant loops that are shown can be chosen based on the size of the window 62D, the number of most relevant loops identified for the code by the loops selection component 50, or other factors. In some embodiments, the number of displayed most relevant loops may be a user-selectable configuration parameter, and/or may be dynamically adjusted based on the size of the confirmation window 62D (optionally including adding or removing loops if/when the window 62D is resized by the user). In some embodiments, if the cardiologist selects one of these loop thumbnails (e.g. using a mouse; hence, the thumbnail serves as the "text" of a hyperlink) then a window pops up which shows the loop as a full resolution video.

With continuing reference to FIGS. 3 and 4, if, at an operation 90, the cardiologist selects a selection button representing one of the preliminary codes, then in an operation 92 code text describing the finding or diagnosis corresponding to the selected preliminary (and now confirmed) diagnostic code is entered into an echocardiogram report. An illustrative report is shown in a window 94D in the illustrative example echocardiogram reading UI display 42D of FIG. 4, where it is diagrammatically indicated that a selection button 96 for the code representing mildly reduced LV performance is selected.

Figure 5:
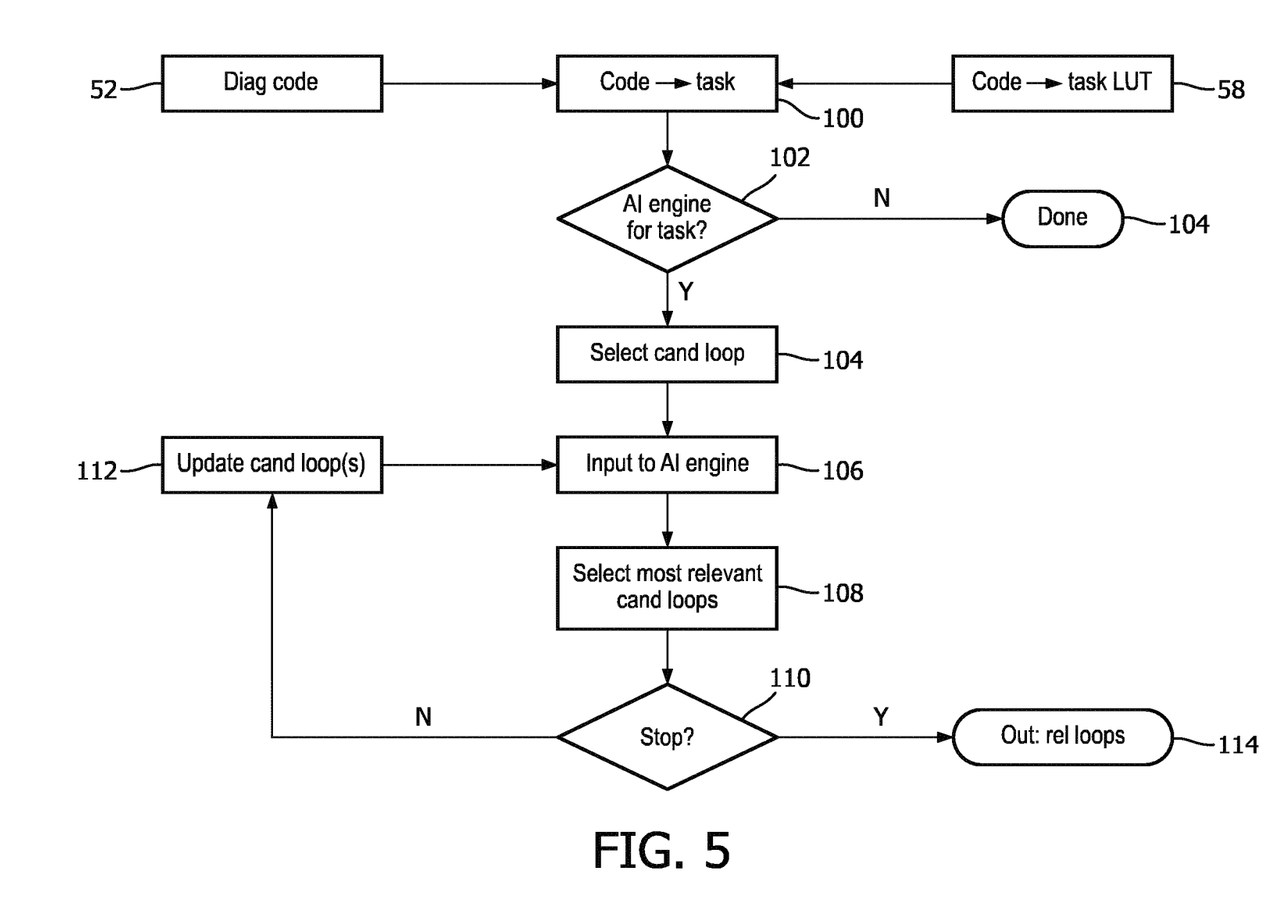
FIG. 5 diagrammatically illustrates a flowchart of a process for identifying or ranking loops of an echocardiogram respective to relevance to a diagnostic code, which is suitably performed by the system of FIG. 1.

With continuing reference to FIG. 1 and with further reference now to FIG. 5, an illustrative example of a method suitably performed by the loops selection component 50 of FIG. 1 for selecting the most relevant loops for the input diagnostic code 52 is shown. In this embodiment, the AI engines 44 include a plurality of different AI engines each trained to perform a specific echocardiogram diagnostic or finding task (e.g., such as the illustrative LV performance assessment task of the illustrative examples herein). Accordingly, in an operation 100, the code-to-task look-up table 58 is referenced to identify the task to which the input code 52 pertains. At an operation 102, it is determined whether the set of AI engines 44 includes an AI engine trained to perform the task identified at 100. If no AI engine is available for this task, then at 104 the loops selection component 50 ends processing for the code 52 without associating any most relevant loops to the code 52. (This may be represented in the loop-up table 60 as a null entry for the code 52, for example). On the other hand, if at the decision operation 102 it is determined that an AI engine trained for the task associated with code 52 is available, then at an operation 104 some candidate loops are selected for testing from the set of echocardiogram loops of the echocardiogram of the patient. For example, in one embodiment, each loop of the echocardiogram is treated in isolation as a candidate loop (e.g., if the echocardiogram comprises 100 loops then initially each of these 100 loops is tested by itself). At an operation 106, each of the loops selected at 104 are input to the AI engine of the AI engines 44 which is trained for the task identified at 102. At an operation 108, the confidence scores returned by the AI engine for the code 52 for each loop (or more generally, for each subset of one or more loops of the echocardiogram selected at 104) is used to identify the most relevant loop (or loop subset) or the N most relevant loops (or N most relevant loop subsets) (where N is some positive integer). At a stopping criterion 110, it is determined whether more testing should be performed. If the stopping criterion 110 is not met, then flow passes to an operation 112 where the candidate loops (or loop subsets) are updated and flow passes back to operation 106 where the updated loops or loop subsets are tested by the AI and at 108 the most relevant of the updated loops are selected, and so on until the stopping criterion 110 is met.

For example, in one approach, the operation 104 selects each individual loop of the echocardiogram for testing. Hence, if there are N loops in the echocardiogram this will generate N tests each consisting of a single loop. In this example, at operation 108 the single loop with the best confidence score is accepted as the most relevant loop. Then, at operation 112, updated loop subsets are generated each of which is a two-loop subset including the accepted most relevant loop and one other loop. So, if there are N loops in the echocardiogram, then this generates N−1 two-loop subsets. Each of these N−1 two-loop subsets is tested as per operation 106, and at the next pass of operation 108 the most relevant two-loop subset is selected. Flow then passes again to operation 112 where each remaining loop is added to this most relevant two-loop subset to generate N−2 three-loop subsets. This process can be continued to identify any chosen number of most relevant loops, e.g. if the stopping criterion 110 stops after this second pass then the final output 114 will be the three most relevant loops to the code 52.

With reference again to FIG. 5, another example of a suitable most relevant loops selection process that may be performed by the loops selection component 50 is as follows. The diagnostic code is mapped onto a family of codes (e.g. an echocardiogram task) at the operation 100. For instance, the code "LV-2: Left ventricular performance is mildly reduced" is mapped onto the family "left ventricular performance". This mapping is suitably performed by way of the lookup table 58. A family may have an AI engine associated with it that is leveraged for loop selection. For any given diagnostic code, if at operation 102 it is determined that there is no AI engine associated with its family, then no loops are selected and the process terminates at 104. On the other hand, if there is an AI engine, then the loop selection component 50 leverages it to select a subset of loops that sufficiently support the diagnostic code. This can be achieved in various ways. In this illustrative example, a gradient ascent selection process is used. In a gradient ascent search, a function F is maximized by iteratively traversing a multi-dimensional grid and picking as successor the node that maximally increases the function score. Here, a node corresponds to a subset of the set of loops of the echocardiogram. In the grid, one can traverse from one node to the next, if the subsets of loops associated with the loops are identical, after adding one loop to either node.

For each node n, the value F(n) is determined by two values that are generated by the AI engine: (1) the likelihood of the inputted diagnostic code (e.g., "LV-2") according to the AI engine; and (2) the confidence score output for that code by the AI engine. The function F combines these inputs to generate one composite value.

In one processing sequence following this approach, the initial iteration starts with an empty set of loops, and the search will find the one loop that is maximally supportive of the likelihood as indicated by the confidence scores output for the individual loops for the inputted diagnostic code (encoded by F). Then, by iteratively adding more and more loops, the likelihood and confidence in the inputted diagnostic code will typically increase. The search can terminate if one of the following criteria (i.e., an illustrative example of the stopping criterion 100) holds: (i) the delta between F(n) and F(n'), where n is the prior node an n' is current node, does not exceed a predetermined threshold; or (ii) whenever F(n) exceeds a predetermined threshold or a threshold that is determined specifically for this search.

In a more generalized workflow, the loops selection component 50 may suitably operate as follows. The diagnostic code 52 is generated (e.g. by the AI engines 44 leveraged to determine preliminary diagnostic codes) or received (e.g. by receiving the diagnostic code via a user input 16 of the echocardiograph 10) for an echocardiogram comprising a set of echocardiogram loops. A plurality of different subsets are selected from the echocardiogram, where each subset consists of one or more echocardiogram loops of the set of echocardiogram loops. For each subset, a confidence score indicating relevance of the subset to the diagnostic code 52 is determined. The confidence score is determined using the AI engine 44 operating on the subset, where the AI engine that determines the confidence score is trained on historical echocardiograms labeled with diagnostic codes. A relevant group of echocardiogram loops is identified based on the determined confidence scores for the respective subsets indicating relevance of the respective subsets to the diagnostic code. An echocardiogram reading user interface 62D (see FIG. 4) is presented, including displaying the diagnostic code associated with the echocardiogram loops of the relevant group of echocardiogram loops.

In this generalized workflow, the echocardiogram analysis method may iterate between the selecting of the subsets and the determining of the confidence scores. In such an iterative embodiment, at least one iteration of the selecting is based at least in part on confidence scores determined for subsets selected in a previous iteration of the selecting.

As another more specific example of this generalized workflow, the selecting of the subsets and the determining of the confidence scores may include: selecting one or more first subsets from the echocardiogram; determining confidence scores for the one or more first subsets indicating relevance of the respective first subsets to the diagnostic code; selecting one or more second subsets by expanding the first subsets with additional echocardiogram loops; and determining confidence scores for the one or more second subsets indicating relevance of the respective first subsets to the diagnostic code. This iterative loop may be continued by further iterations of selecting one or more further (e.g. third) subsets by expanding the (last, e.g. second) subsets with additional echocardiogram loops; and determining confidence scores for the one or more further (e.g. third) subsets indicating relevance of the respective third subsets to the diagnostic code.

In presenting the echocardiogram reading user interface 42, this may include displaying the echocardiogram report (e.g. via window 94D of FIG. 4). Responsive to receiving a user selection of one of the echocardiogram loops of the relevant group of echocardiogram loops via (the confirmation window 62D of) the echocardiogram reading user interface 42D, the user selected echocardiogram loop is displayed. Responsive to receiving a user selection confirming the diagnostic code via (the confirmation window 62D of) the echocardiogram reading user interface 42D, text corresponding to the diagnostic code is inserted into the echocardiogram report.

Optionally, echocardiogram analysis method further includes ranking the echocardiogram loops of the relevant group of echocardiogram loops based on the determined confidence scores for the respective subsets. In this case, the echocardiogram loops of the relevant group of echocardiogram loops may be associated with the diagnostic code (e.g. in the confirmation window 62D display) ordered by the ranking.

In another approach for ordering the displayed most relevant loops, for each echocardiogram loop of the relevant group of echocardiogram loops, a loop confidence score indicating relevance of the echocardiogram loop to the diagnostic code is determined using the AI engine operating on the echocardiogram loop. In this approach, the echocardiogram loops of the relevant group of echocardiogram loops are associated with the diagnostic code ordered by the loop confidence scores.

In the illustrative examples, each AI engine 44 comprises an artificial neural network (ANN). However, more generally the AI engines 44 can be any type of classifier that outputs a confidence score for a diagnostic code in response to processing an echocardiogram loop or subset of loops. As some non-limiting illustrative examples, the one or more AI engines 44 could include one or more of: an ANN trained on historical echocardiograms labeled with diagnostic codes; a Support Vector Machine (SVM) trained on historical echocardiograms labeled with diagnostic codes; another type of machine learning (ML) component trained on historical echocardiograms labeled with diagnostic codes; a logistic regression classifier trained on historical echocardiograms labeled with diagnostic codes; or so forth.

The invention has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A non-transitory storage medium storing instructions readable and executable by an electronic processor to perform an echocardiogram analysis method including:
generating or receiving a preliminary diagnostic code for an echocardiogram comprising a set of echocardiogram loops, the diagnostic cod being a unique identifier a certain diagnosis of finding;
selecting a plurality of different subsets from the echocardiogram wherein each subset consists of one or more echocardiogram loops of the set of echocardiogram loops;
for each subset, determining a confidence score indicating relevance of the subset to the diagnostic code wherein the confidence score is determined using an artificial intelligence (AI) engine operating on the subset, wherein the AI engine is trained on historical echocardiograms comprising echocardiogram loops and being labeled with diagnostic codes, wherein one or more candidate loops are input to the AI engine and the AI engine outputs the diagnostic code and the confidence score for the diagnostic code;
identifying a relevant group of echocardiogram loops based on the determined confidence scores for the respective subsets indicating relevance of the respective subsets to the diagnostic code; and
presenting an echocardiogram reading user interface including displaying the diagnostic code associated with the echocardiogram loops of the relevant group of echocardiogram loops.

2. The non-transitory storage medium of claim 1 wherein:
the echocardiogram analysis method includes iterating between the selecting and the determining; and
at least one iteration of the selecting is based at least in part on confidence scores determined for subsets selected in a previous iteration of the selecting.

3. The non-transitory storage medium of claim 1 wherein the selecting and the determining include:
selecting one or more first subsets from the echocardiogram;
determining confidence scores for the one or more first subsets indicating relevance of the respective subsets to the diagnostic code;
selecting one or more second subsets by expanding the first subsets with additional echocardiogram loops; and
determining confidence scores for the one or more second subsets indicating relevance of the respective second subsets to the diagnostic code.

4. The non-transitory storage medium of claim 1, wherein the presenting of the echocardiogram reading user interface further includes:
displaying an echocardiogram report;
responsive to receiving a user selection of one of the echocardiogram loops of the relevant group of echocardiogram loops via the echocardiogram reading user interface, displaying the user selected echocardiogram loop;
responsive to receiving a user selection confirming the diagnostic code via the echocardiogram reading user interface, inserting text corresponding to the diagnostic code into the echocardiogram report.

5. The non-transitory storage medium of claim 1 wherein the echocardiogram analysis method further includes:
ranking the echocardiogram loops of the relevant group of echocardiogram loops based on the determined confidence scores for the respective subsets;
wherein the echocardiogram loops of the relevant group of echocardiogram loops are associated with the diagnostic code ordered by the ranking.

6. The non-transitory storage medium of claim 1 wherein the echocardiogram analysis method further includes:
for each echocardiogram loop of the relevant group of echocardiogram loops, determining a loop confidence score indicating relevance of the echocardiogram loop to the diagnostic code wherein the loop confidence score is determined using the AI engine operating on the echocardiogram loop; and
wherein the echocardiogram loops of the relevant group of echocardiogram loops are associated with the diagnostic code ordered by the loop confidence scores.

7. The non-transitory storage medium of claim 1 wherein the generating or receiving of the diagnostic code includes:
automatically generating the diagnostic code using the AI engine operating on subsets of the set of echocardiogram loops.

8. The non-transitory storage medium of claim 1 wherein the generating or receiving of the diagnostic code includes:
acquiring the echocardiogram comprising the set of echocardiogram loops using an echocardiograph; and
receiving the diagnostic code via a user input of the echocardiograph.

9. The non-transitory storage medium of claim 1 wherein the AI engine comprises an artificial neural network.

10. The non-transitory storage medium of claim 1 wherein:
the AI engine comprises a plurality of task-specific AI engines each trained on historical echocardiograms labeled with diagnostic codes for a corresponding clinical task, and
the confidence score indicating relevance of the subset to the diagnostic code is determined by identifying a clinical task to which the diagnostic code corresponds and using the task-specific AI engine for the identified clinical task operating on the subset.

11. An echocardiogram analysis device comprising:
an electronic processor; and
a non-transitory storage medium storing instructions readable and executable by the electronic processor to analyze an echocardiogram comprising a set of echocardiogram loops, the stored instructions including:
AI engine instructions implementing an artificial intelligence (AI) engine trained to output confidence levels for diagnostic codes in response to receiving an input set of one or more echocardiogram loops;
relevant loops identification instructions implementing a relevant loops identification including determining confidence levels for a preliminary diagnostic code, the diagnostic code being a unique identifier to a certain diagnosis or finding, for different subsets of the set of echocardiogram loops by inputting the different subsets to the AI engine and identifying a relevant group of echocardiogram loops based on the determined confidence scores for the respective subsets; and
echocardiogram reading instructions implementing an echocardiogram reading user interface on a client system including displaying, on a display of the client system, the preliminary diagnostic code associated with the echocardiogram loops of the relevant group of echocardiogram loops.

12. The echocardiogram analysis device of claim 11 wherein the relevant loops identification includes (i) initially selecting different subsets, (ii) determining confidence levels for the preliminary diagnostic code for the different subsets by inputting the different subsets to the AI engine, and (iii) at least one iteration of selecting additional subsets by adding echocardiogram loops to the subsets having the highest confidence levels determined in step (ii) and then repeating step (ii) for the additional subsets.

13. The echocardiogram analysis device of claim 11 wherein the implementing of the echocardiogram reading user interface includes:
displaying an echocardiogram report on the display of the client system; and
responsive to receiving a user selection confirming the preliminary diagnostic code via the echocardiogram reading user interface, inserting text corresponding to the preliminary diagnostic code into the echocardiogram report.

14. The echocardiogram analysis device of claim 11 wherein the echocardiogram analysis method further includes:
ranking the echocardiogram loops of the relevant group of echocardiogram loops based on confidence scores for the preliminary diagnostic code determined by inputting subsets of the relevant group of echocardiogram loops to the AI engine;
wherein the echocardiogram loops of the relevant group of echocardiogram loops are associated with the preliminary diagnostic code ordered by the ranking.

15. The echocardiogram analysis device of claim 11 wherein the instructions further include:
analysis instructions for generating the preliminary diagnostic code by operations including inputting subsets of one or more echocardiogram loops of the set of echocardiogram to the AI engine.

* * * * *